United States Patent [19]

Nardella

[11] 4,348,179
[45] Sep. 7, 1982

[54] ADJUSTABLE ORTHODONTIC SCREW ASSEMBLY

[75] Inventor: Alessandro Nardella, Oberhausen, Fed. Rep. of Germany

[73] Assignee: Francesco Pedrazzini, Munich, Fed. Rep. of Germany

[21] Appl. No.: 259,579

[22] Filed: May 1, 1981

[51] Int. Cl.³ .............................................. A61C 7/00
[52] U.S. Cl. ...................................................... 433/7
[58] Field of Search ........................................... 433/7

[56] References Cited

U.S. PATENT DOCUMENTS 3,454,001  7/1969  Stockfisch .............................. 433/7

FOREIGN PATENT DOCUMENTS 1250054  9/1967  Fed. Rep. of Germany .......... 433/7

Primary Examiner—Robert Peshock
Attorney, Agent, or Firm—John C. Dorfman

[57] ABSTRACT

An adjustable orthodontic screw assembly adapted to regulate the position of human teeth comprises two limbs (1a, 1b), the adjacent first ends of said limbs being articulated together, the limbs each being adapted to be embedded in an associated part of a two-part extension plate (16), the second end of each limb having attached thereto a rotatable head member (2a, 2b), each head member being provided with a threaded hole with the threads of the threaded holes of the two head members being of opposite hand. A twin screw (4b) is in threaded engagement with the threaded holes of said rotatable head members. According to the invention, also the first end of either of said limbs (1a, 1b) has attached thereto a rotatable head member (2c, 2d) provided with a threaded hole, the threaded holes of these two head members being of opposite hand. A second twin screw (4a) is in threaded engagement with the threaded holes of the head members (2c, 2d) attached to the first ends of said limbs (1a, 1b).

6 Claims, 8 Drawing Figures

ADJUSTABLE ORTHODONTIC SCREW ASSEMBLY

This invention relates to an adjustable orthodontic screw assembly for regulating the position of human teeth.

Such an adjustable orthodontic screw assembly has already been disclosed in an advertising leaflet published by the firm Alessandro Pozzi, Florence, Italy. In said leaflet, said assembly is termed Model Leone No. 515 and 516 fan type screw assembly.

If it is necessary, for the purpose of correcting the position of the teeth of a patient, to spread or extend the arch formed by the teeth, the first step consists in fitting to the teeth an extension plate contacting the inner side of the teeth. Following this, the extension plate is cut in half, whereupon the two halves are interconnected by means of the screw assembly. As the extension of the jaw is progressing, the screw assembly is spread to an ever increasing extent so that pressure is constantly exerted on the inner sides of the teeth.

In view of the fact that the aforementioned known screw assembly can be adjusted on one side only, this being the side on which the twin screw is located, certain limitations arise in respect of the use of the assembly. More in particular, the known screw assembly is not adapted to exert pressure on the teeth in a forward or rearward direction as it would be desired; as a result, it soon becomes necessary to employ additional means such as clamps and the like, and in the course of the orthodontic treatment it will become necessary to repeat the fitting and employment of modified extension plates.

In view of the foregoing, it is an object of this invention to provide a screw assembly which can be used in the most versatile manner possible and which is adapted not only to force the teeth apart at the front and/or rear mostly in a transverse direction but which is also adapted to exert forwardly or rearwardly directed forces on the teeth.

According to the invention, this object is attained by attaching also to each of the first ends of said limbs a rotatable head member provided with a threaded hole with the threads of the threaded holes being of opposite hand, and by providing a second twin screw which is in threaded engagement with the threaded holes of the head members attached to the first ends of the limbs.

In view of the fact that in an adjustable transversally acting screw assembly of the invention the limbs may be adjusted at both ends thereof, it is possible, after constructing and fitting an extension plate, to employ the extension plate throughout the duration of an orthodontic treatment. The screw assembly of the invention makes it possible not only to exert independent transverse forces on the front and/or rear teeth but also to provide a forwardly or rearwardly directed pressure component.

More specifically, the adjustable orthodontic screw assembly of the present invention, which is adapted to regulate the position of human teeth, is fixed to or partially embedded in a two part extension plate, the separate parts of which are formed to fit against teeth supporting gums on opposite sides of one of the jaws. Rather than being a single molded plate, the plate is formed in two parts which may advantageously be symmetrical halves designed to cooperate with the two supporting gums on one side of one jaw with the plates being separated sufficiently to enable the screw assembly to fit between them and to thereby adjust the relative positions of the two plate parts. The screw assembly itself consists of two limbs each secured to one of the extension plate parts by suitable form of attachment including molding into the part, limbs extending along the length of the separation between the plates between the plate parts. Means is provided to articulate together the limbs at selected first opposed points. At second opposed points spaced from the first opposed points on each limb, a head member is rotatably supported on each limb so that the respective head members rotate about generally parallel axes. Each head member is provided with a threaded hole transverse to the axis of rotation with the threads of the threaded holes of the two head members being of opposite hand. A twin screw has opposite ends oppositely threaded for engagement with the threaded holes of the respective rotatable head members. As the consequence of this arrangement, when the twin screw is rotated in one direction, the limbs move apart and when the twin screw is rotated in the opposite direction, the limbs move together, any relative rotation of the limbs being accommodated by the respective rotatable head members. The articulation of the limbs at the first opposed points is also provided by rotatable head members similar to those at the second points and a second twin screw. The limbs are advantageously respectively embedded in a different one of the separate plate members as they are molded. The limbs may be constructed so as to provide bifurcated supports for the rotatable head members whereby the head members are engaged at opposite ends along their axis of rotation to provide suitable bearings. Preferably, also the twin screws are provided with operating members in the form of coaxial cylindrical bodies, preferably provided with radial holes to permit insertion of lever means to turn the twin screws.

The invention will now be explained in further detail, reference being had to the accompanying drawings in which.

Figure 4:
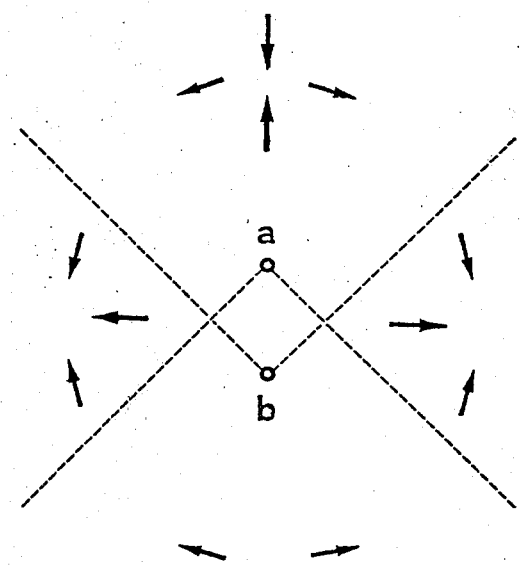

FIG. 4 indicates diagrammatically the forces capable of being exerted on human teeth by means of a screw assembly of the invention; and FIGS. 5 to 8 diagrammatically show examples of the capabilities of the screw assembly of the invention.

Figure 1:
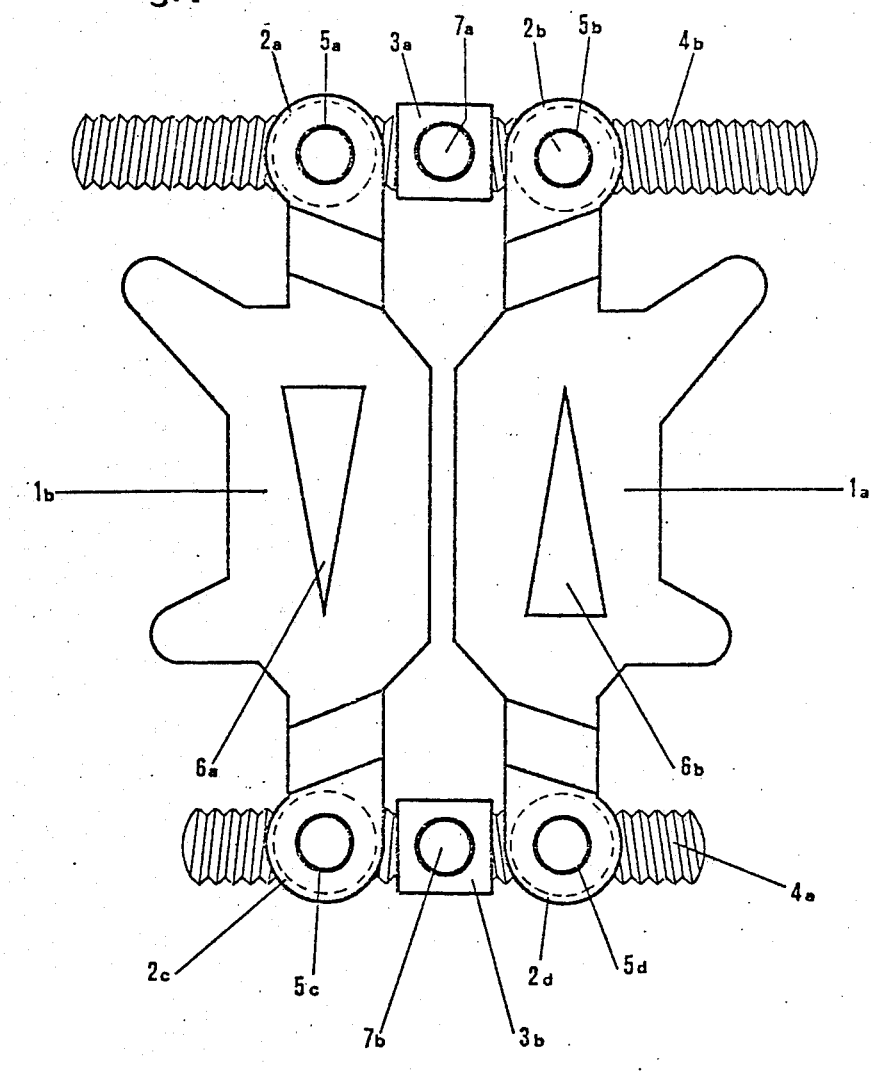
FIG. 1 shows an elevation of a screw assembly of the invention.
Figure 2:
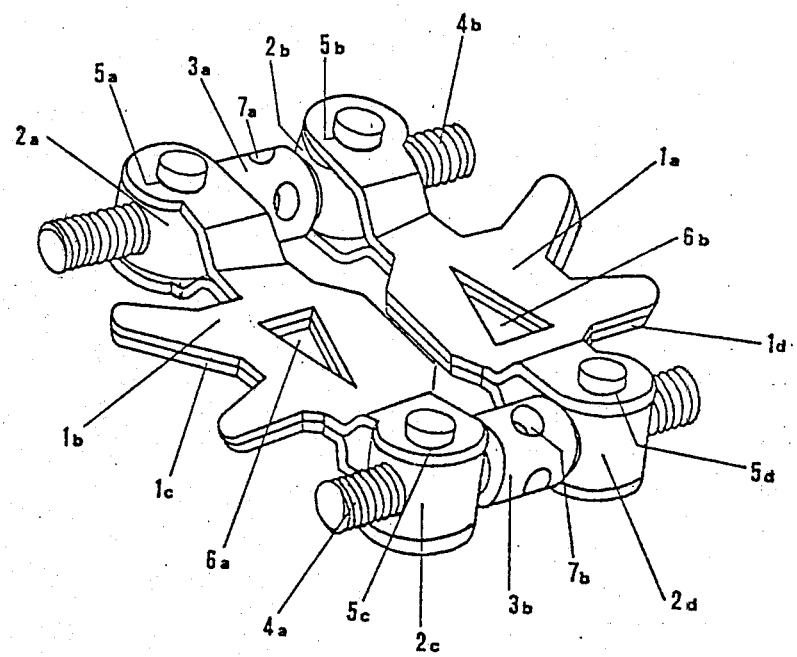
FIG. 2 shows an isometric view of the screw assembly of FIG. 1.

As shown in FIGS. 1 and 2, each of the limbs of the screw assembly includes two superimposed sheet-metal members $1a$, $1d$ and $1b$, $1c$, respectively. These sheet-metal members, each of which is provided with a directional arrow $6a$ or $6b$, respectively, have bifurcated ends which are each provided with a rotatable head member $2b$, $2d$ and $2a$, $2c$, respectively. The ends of the sheet-metal members $1a$, $1b$, $1c$ and $1d$ are each provided with a bore, and in these bores there are supported for rotation bearing pins $5a$, $5b$, $5c$ and $5d$ with which the rotatable head members $2a$, $2b$, $2c$ and $2d$ are provided.

The rotatable head members $2a$, $2b$ and $2c$, $2d$ are respectively provided with threaded holes of opposite hand which are in threaded engagement with a twin screw $4a$ and $4b$, respectively. The portions of the two twin screws $4a$ and $4b$ extending between the rotatable head members associated therewith are each provided with an operating member 3b and 3a, respectively, which are respectively provided with radial holes 7b and 7a.

Rotation of the twin screws 4a and 4b will cause the rotatable head members 2c, 2d and 2a, 2b, respectively, together with the associated ends of the limbs 1a, 1d and 1b, 1c, to be either spread apart or drawn together. The twin screws 4a and 4b may be rotated by means of a piece of plain wire which can be inserted into the radial holes 7a or 7b.

Figure 3:
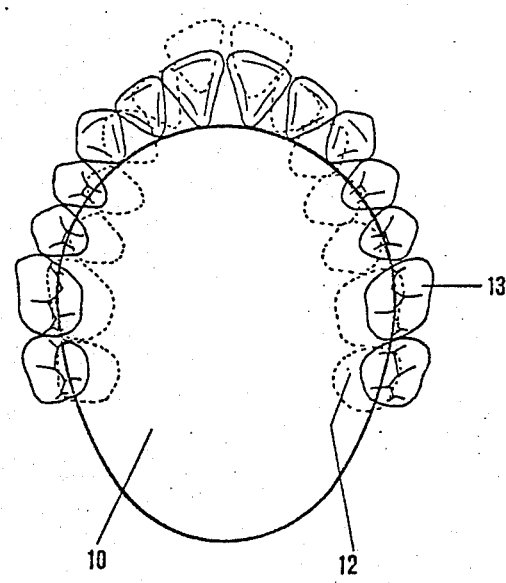
FIG. 3 is a schematic representation of an anomalous and of a healthy set of teeth.

FIG. 3 shows in dotted lines an anomalous set of teeth 12 and in full lines a healthy or corrected set of teeth, the shape of which corresponds to the ideal egg shape 10.

FIG. 4 shows (with the exception of the arrows extending vertically upwardly and downwardly, respectively) the forces which may be exerted on the anomalous set of teeth 12 shown in FIG. 3 by means of the screw assembly of the invention.

Figure 5:
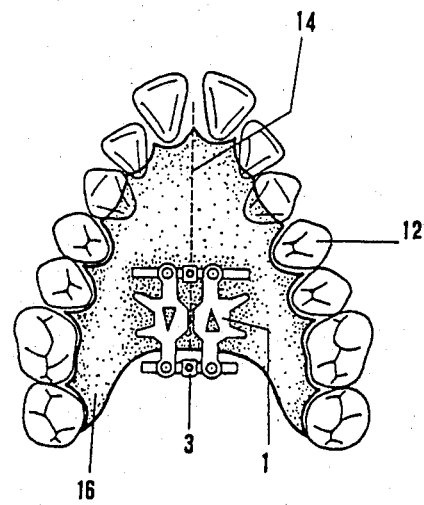
Figure 6:
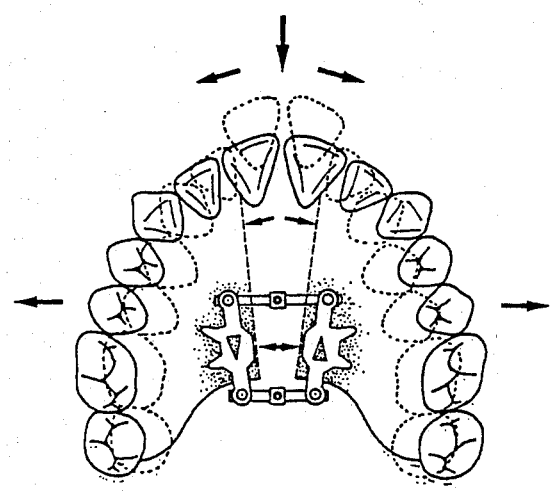

FIGS. 5 and 6 illustrate the use of the screw assembly of the invention at the beginning and at the end, respectively, of a set of teeth subjected to orthodontic treatment. The two halves 16 of the extension plate which have been separated by a saw cut 14 are interconnected by means of the screw assembly of the invention, and the operating members 3a and 3b of the twin screws 4b and 4a, respectively, may be rotated so as to spread apart the parts of the extension plate at the front and/or rear to a smaller or greater extent. For the purpose of effecting additional corrections, it is possible, for example, to employ a filing tool by means of which the external edges of the extension plate parts contacting the inner surfaces of the teeth may be given the desired shape. It is possible to spread apart the teeth to a greater or lesser extent at the front and the rear and also to exert forwardly or rearwardly directed pressure components on the teeth.

Figure 7:
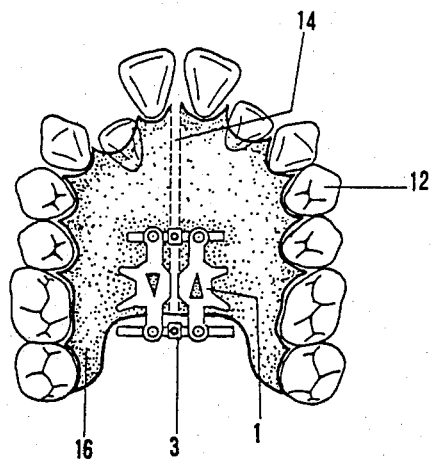
Figure 8:
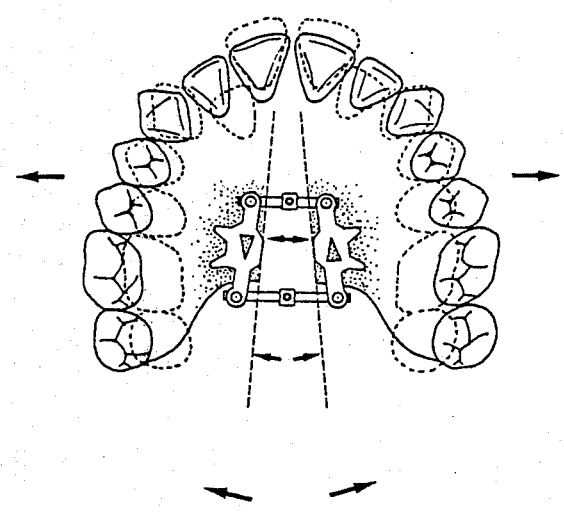

FIGS. 7 and 8 also illustrate the use and the effect of the screw assembly of the invention at the beginning of a orthodontic treatment and towards the end of the treatment, it being seen that at the beginning the two second incisors had been seriously displaced to the rear. Also these illustrations show that it is possible by means of the screw assembly of the invention to force apart the front teeth on the one hand and the rear teeth on the other in a completely independent manner so that the second incisors may be displaced forwardly by means of suitable inserts, such inserts being introduced as soon as sufficient space for the reception of the second incisors has been provided in the jaw.

Summarizing the above description, it may be stated that the advantage of the twin fan type screw assembly of the invention resides in the fact that the assembly makes it possible to select any desired variation in respect of a transverse extension at the front and rear teeth, respectively, without it becoming necessary to employ a plurality of different screw assemblies. Another advantage is to be seen in the fact that the screw assembly of the invention makes it possible to expedite the orthodontic treatment, whereas the known screw assembly described earlier is only adapted to perform a certain part of the treatment.

What is claimed is:

1. An adjustable orthodontic screw assembly adapted to regulate the position of human teeth comprising:
   a two-part extension plate, the separate parts being formed to fit against teeth-supporting gums on opposite sides of one of the jaws, the two parts of the plates being separated and held together by the screw assembly which includes
   two limbs each secured to one of the extension plate parts and extending along the length of the separation between the plate parts,
   means articulating together said limbs at selected first opposed points, second opposed points spaced from the first opposed points on each limb supporting a head member rotatable respectively about parallel axes, each head member being provided with a threaded hole transverse to the axis of rotation with the threads of the threaded holes of the two head members being of opposite hand,
   a twin screw having opposed ends oppositely threaded for threaded engagement with the threaded holes of said respective rotatable head members, whereby as the twin screw is rotated in one direction the limbs move apart and as the twin screw is rotated in the opposite direction the limbs move together any relative rotation of the limbs being accommodated by the respective rotatable head members.

2. The adjustable orthodontic screw assembly of claim 1 in which the articulation at the first opposed points of the limbs is provided by head members of the type provided at the second opposed points and with a similar twin screw engageable in the oppositely threaded holes of said head members.

3. The adjustable orthodontic screw assembly of claim 1 or 2 in which each of the limbs is secured to one of the extension plates by being partially embedded in that plate.

4. The adjustable orthodontic screw assembly of claim 1 or 2 in which each head member is supported at opposed axial ends by bifurfacted portions of the supporting limb the suitable structure to permit rotation.

5. The adjustable orthodontic screw assembly of claim 1 or 2 in which the limbs are made of laminated sheet metal parts spaced apart at the first and second points to rotatably support the respective head members to permit their rotation about parallel axes.

6. The adjustable orthodontic screw assembly of claim 1 or 2 in which coaxial cylindrical operating members are provided between the respective threaded portions of the twin screw and provided with generally radial holes whereby lever means may be inserted to rotate said twin screw.

* * * * *